(12) United States Patent
Forster

(10) Patent No.: US 9,317,795 B2
(45) Date of Patent: Apr. 19, 2016

(54) ARRAY OF RFID TAGS WITH SENSING CAPABILITY

(75) Inventor: Ian James Forster, Essex (GB)

(73) Assignee: Avery Dennison Corporation, Glendale, CA (US)

( * ) Notice: Subject to any disclaimer, the term of this patent is extended or adjusted under 35 U.S.C. 154(b) by 459 days.

(21) Appl. No.: 13/287,235

(22) Filed: Nov. 2, 2011

(65) Prior Publication Data

US 2013/0106578 A1  May 2, 2013

(51) Int. Cl.
| | |
|---|---|
| H04Q 5/22 | (2006.01) |
| G08B 21/00 | (2006.01) |
| G08B 13/14 | (2006.01) |
| G08B 23/00 | (2006.01) |
| G08B 25/00 | (2006.01) |
| B60K 28/00 | (2006.01) |
| G01G 23/36 | (2006.01) |
| G06K 19/07 | (2006.01) |
| A61B 5/00 | (2006.01) |

(52) U.S. Cl.
CPC ............ *G06K 19/0717* (2013.01); *A61B 5/447* (2013.01); *A61B 5/6891* (2013.01); *A61B 2562/0247* (2013.01); *A61B 2562/066* (2013.01)

(58) Field of Classification Search
CPC .................. A61M 27/006; A61M 2205/6072; A61M 5/03; G08B 23/00
USPC ........................................ 340/10.4
See application file for complete search history.

(56) References Cited

U.S. PATENT DOCUMENTS

| | | | |
|---|---|---|---|
| 6,275,157 B1 * | 8/2001 | Mays et al. ................ | 340/572.5 |
| 6,720,866 B1 * | 4/2004 | Sorrells et al. ............... | 340/10.4 |
| 7,026,941 B1 | 4/2006 | Anderson | |
| 7,369,948 B1 | 5/2008 | Ferenczi et al. | |
| 2004/0087231 A1 * | 5/2004 | Nakanishi et al. ............ | 442/179 |
| 2005/0046584 A1 * | 3/2005 | Breed ....................... | 340/825.72 |
| 2006/0038684 A1 | 2/2006 | Lahiri | |
| 2006/0110998 A1 * | 5/2006 | Takenishi et al. ............. | 442/110 |
| 2007/0013517 A1 * | 1/2007 | Posamentier ............... | 340/572.1 |
| 2007/0046435 A1 * | 3/2007 | Fratti et al. ................... | 340/10.2 |

(Continued)

FOREIGN PATENT DOCUMENTS

| | | |
|---|---|---|
| DE | 19645083 | 5/1998 |
| DE | 102009005100 | 7/2010 |

OTHER PUBLICATIONS

International Preliminary Report on Patentability issued in corresponding IA No. PCT/US2012/063185 dated May 6, 2014.

(Continued)

*Primary Examiner* — Andrew Bee
*Assistant Examiner* — Pameshanand Mahase
(74) *Attorney, Agent, or Firm* — Avery Dennison Corporation

(57) ABSTRACT

An RFID sensing system and method. An array of sensing elements is disposed on a surface of a mat, wherein each sensing element includes an RFID microchip, an antenna operatively coupled to the microchip, and a pressure-sensitive material disposed on at least the antenna. An RFID reader is provided for interrogating the array of sensing elements. An antenna operatively coupled to the reader communicates with each sensing element disposed on the mat. Each sensing element in the array, in response to an interrogation signal, transmits a signal to the reader via the coupled antenna when a subject placed on the mat compresses the section of pressure-sensitive material for the sensing element.

44 Claims, 7 Drawing Sheets

(56) References Cited

U.S. PATENT DOCUMENTS

| | | |
|---|---|---|
| 2007/0057790 A1 | 3/2007 | Alden et al. |
| 2007/0057792 A1* | 3/2007 | Alden .................. 340/572.1 |
| 2007/0143006 A1 | 6/2007 | Plettner |
| 2007/0268112 A1* | 11/2007 | Watanabe .............. G01D 21/00 340/10.1 |
| 2008/0120784 A1* | 5/2008 | Warner et al. .................. 5/658 |
| 2008/0126132 A1 | 5/2008 | Warner et al. |
| 2008/0230866 A1 | 9/2008 | Kulp |
| 2009/0058661 A1* | 3/2009 | Gleckler et al. .......... 340/573.7 |
| 2009/0096589 A1 | 4/2009 | Kuehl et al. |
| 2009/0243833 A1 | 10/2009 | Huang et al. |
| 2010/0063778 A1* | 3/2010 | Schrock et al. ............... 702/188 |
| 2010/0156640 A1* | 6/2010 | Forster ...................... 340/572.1 |
| 2010/0225482 A1 | 9/2010 | Kasai et al. |
| 2010/0252627 A1 | 10/2010 | Perkins et al. |
| 2010/0258334 A1* | 10/2010 | Akaike et al. ............. 174/126.1 |

OTHER PUBLICATIONS

International Search Report and Written Opinion issued in corresponding IA No. PCT/US2012/063185 dated Feb. 4, 2013.

* cited by examiner

ARRAY OF RFID TAGS WITH SENSING CAPABILITY

TECHNICAL FIELD

Embodiments of the invention relate generally to measuring parameters such as pressure and temperature using radio frequency identification technology.

BACKGROUND OF THE INVENTION

Radio-frequency identification (RFID) is a generic term for technologies that use radio waves to automatically identify objects. There are several conventional methods of identifying objects using RFID, the most common of which is to store a serial number and other information that identifies a product on a microchip that is attached to an antenna. The chip and the antenna together define an RFID transponder circuit that is referred to as an RFID tag or RFID label. The tag is very thin and flexible and can include an etched antenna and a miniature chip with a memory for storage of data. The antenna enables a remote reader that has a transceiver to communicate with the chip, and enables the chip to transmit identification information back to the reader when actuated to do so by the reader. The reader converts the radio waves returned from the RFID tag into a form that can then be utilized by a computer.

RFID tags are classified into three different types: active, semi-active, and passive. Active and semi-active tags include a battery to power the microchip. While passive tags are remotely-powered, active tags broadcast their information. Passive tags are the most frequently used since they have a low cost of production and are easily used. Low frequency RFID systems (125-148 kHz) and high frequency RFID systems (13.56 MHz) have short transmission ranges up to 1 meter. Ultra-high frequency (UHF) RFID systems (902-928 MHz) can cover a range up to 10 meters. Microwave frequency RFID systems (2.45 GHz) cover transmission ranges up to 30 meters.

Traditionally, RFID tags have been used for wireless tracking of goods in the retail industry to deal with the problem of inventory management and to act as a theft deterrent. More recently, new applications of RFID technology have been investigated, including the use of RFID tags as sensors to measure parameters such as temperature. When detecting a signal, the sensor produces a measureable output, typically a voltage or current that is related to the signal.

SUMMARY OF THE INVENTION

Embodiments of the invention measure parameters such as pressure and/or temperature over a large area for medical or other wide area footprint applications requiring a robust solution with inherent redundancy. In one embodiment, an array of radio frequency identification (RFID) tags is interrogated by an RFID sensor system, either via a far field or a near field antenna. Alternatively, interrogation can occur via a transmission line structure built into a mat or other device. Sensing can be achieved by altering a characteristic of the RFID device or by using RFID chips with a sensor port, such as one capable of measuring resistance, whereupon the sensed data is contained in messages from the tag device.

In one embodiment, an RFID sensing system includes an array of sensing elements disposed on a surface of a mat, wherein each sensing element includes an RFID microchip, an antenna operatively coupled to the microchip, and a pressure-sensitive material disposed on at least the antenna. An RFID reader is provided for interrogating the array of sensing elements. An antenna operatively coupled to the reader communicates with each sensing element disposed on the mat. Each sensing element in the array, in response to an interrogation signal, transmits a signal to the reader via the coupled antenna when a subject placed on the mat compresses the pressure-sensitive material for the sensing element.

In another embodiment, an RFID sensing system includes an array of sensing elements disposed on a surface of a mat, wherein each sensing element includes an RFID microchip, an antenna operatively coupled to the microchip, and a pressure-sensitive material disposed on at least the antenna. An RFID reader is provided for interrogating the array of sensing elements. A transmission line is coupled to a port of the reader and to each element in the array of sensing elements. Each sensing element in the array, in response to an interrogation signal, transmits a signal to the reader via the coupled transmission line when a subject placed on the mat compresses the pressure-sensitive material for the sensing element.

In a further embodiment, an RFID sensing system includes an array of sensing elements disposed on a surface of a mat, wherein each sensing element includes an RFID microchip, an antenna operatively coupled to the microchip, and a pressure-sensitive material disposed on at least the antenna. A multi-port RFID reader is provided for interrogating the array of sensing elements. A plurality of transmission lines are coupled to separate ports of the reader and to an associated plurality of elements in the array of sensing elements. Each sensing element in the array, in response to an interrogation signal, transmits a signal via the transmission line when a subject placed on the mat compresses the pressure-sensitive material.

In a further embodiment, an RFID sensing system includes an array of sensing elements disposed on a surface of a mat, wherein each sensing element includes an RFID microchip, an antenna operatively coupled to the microchip, and a pressure-sensitive material disposed on at least the antenna. An RFID reader is provided for interrogating the array of sensing elements. A fixed near field coupler disposed in proximity to the mat links the array of sensing elements with the reader via a transmission line disposed on the mat. Each sensing element in the array, in response to an interrogation signal, transmits a signal to the reader via the transmission line and near field coupler when a subject placed on the mat compresses the section of conductive foam for the sensing element.

BRIEF DESCRIPTION OF THE DRAWINGS

These and other advantages and aspects of the embodiments of the disclosure will become apparent and more readily appreciated from the following detailed description of the embodiments taken in conjunction with the accompanying drawings, as follows.

DETAILED DESCRIPTION OF THE EMBODIMENT

The following description is provided as an enabling teaching of embodiments of the invention including the best, currently known embodiment. Those skilled in the relevant art will recognize that many changes can be made to the embodiments described, while still obtaining the beneficial results. It will also be apparent that some of the desired benefits of the embodiments described can be obtained by selecting some of the features of the embodiments without utilizing other features. Accordingly, those who work in the art will recognize that many modifications and adaptations to the embodiments described are possible and may even be desirable in certain circumstances. Thus, the following description is provided as illustrative of the principles of the embodiments of the invention and not in limitation thereof, since the scope of the invention is defined by the claims.

In an exemplary embodiment, an array of sensor-equipped tags (sensing elements) can be used to sense parameters, for example, the weight distribution of a person lying in bed, temperature, or other factors. Each RFID device acts as a node and the tags are read by an RFID reader, either by illuminating the entire array, or by using a transmission line structure to deliver an RF field to each node. The sensor effect on the node could be: (1) a physical parameter of the communication between the reader and the RFID node, such as sensitivity, (2) the frequency response related to sensitivity, (3) backscatter signal strength, (4) frequency response of backscatter signal strength, (5) relative levels of upper and lower sidebands when the signal from a node is coherently detected, or (6) a separately sensed value, where a characteristic of the data communication, such as the data rate or data content is retrieved from a specified memory location or value on a port.

Since the cost of individual RFID chips continues to fall, using a large array of RFID tags, for example, a 20×50 array, is practical for a number of applications. In several examples described herein, pressure can be measured over a large area associated with a patient lying on a bed. Excessive pressure at a point is associated with the formation of a pressure ulcer, which is both unpleasant for the patient and expensive to treat, and can contribute to a fatal outcome. A pressure ulcer is an area of skin that breaks down when constant pressure is placed against the skin.

Figure 1:
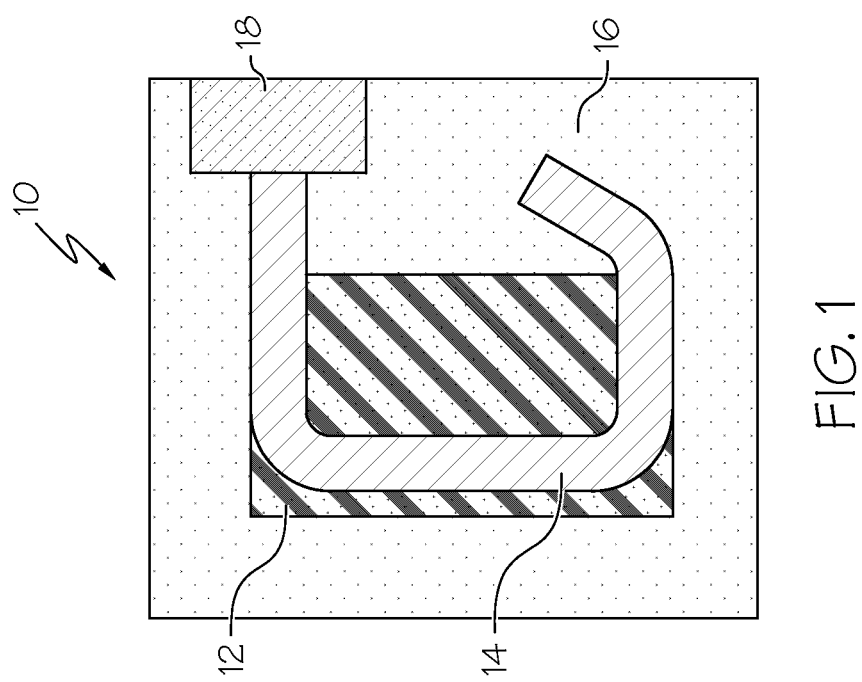
FIG. 1 illustrates a simple structure for a pressure sensitive RFID tag device in an exemplary embodiment.

FIG. 1 illustrates a simple structure for a pressure-sensitive RFID tag device 10 in an exemplary embodiment. The pressure-sensitive RFID tag device 10 is also referred to herein alternatively, as a sensing element and a sensor device. The structure 10 uses a small 16 mm$^2$ UHF antenna design including a slot with an RFID chip 18 or strap attached across the open end. The antenna 14 is defined by conductive material such as die cut aluminum, printed conductive ink, or etched copper/aluminum. The structure 10 can be loaded by a section of foam 12 that is coated with or contains conductive particles such as carbon. A layer of adhesive overlaminate material can be applied to separate the conductive material from the section of foam. For example, a PET overlaminate of 12.5 μm thickness can be used. When the section of foam 12 is compressed, the resistance of the material drops. As the section of foam 12 is coupled to the antenna 14, the change in resistance causes energy to be absorbed at the operating frequency of the tag 10 thus changing its sensitivity. This change can be determined with a UHF RFID reader by altering the output power and determining the power level at which the identifier (ID) associated with this sensing device 10 starts to read, and hence the pressure at that point can be measured.

The sensitivity of an RFID tag is determined by a number of factors, including the dielectric and magnetic properties of the materials in proximity to the antenna. In the embodiment of FIG. 1, the resistivity of the foam is a function of the pressure and is coupled to the antenna in such a way that when the RFID tag is exposed to an RE field some of the energy is dissipated in the foam material, reducing the amount of energy available to the RF device, hence altering its sensitivity. For example, if at a given pressure, one half of the incident energy is dissipated by the pressure dependent resistivity of the foam material, the sensitivity of the RFID tag measured remotely will drop by 3 dB.

The thickness and other characteristics of the foam 12 are dependent on the design of the antenna 14 and the rest of the system. Although shown in the embodiment of FIG. 1, the laminate 16 separating the conductive material from the section of foam is not required. The laminate 16 provides the advantage of protecting the RFID tag 10 from the environment. However, in another embodiment, the foam 12 could be in direct contact with the antenna 14, and the whole structure could then be overlaminated.

Conductive foam is simply one example of a material that can have a pressure-dependent characteristic that will interact with RFID. Alternatives to a resistive foam would be to use foam loaded with a dielectric or magnetic material. In this case, compression would alter the frequency response of the RFID tag, which can be measured by taking the threshold at a set of frequencies. Alternatively, fabrics and non-woven materials with printed or coated materials could be used.

Another alternative to conductive foam is a quantum tunneling composite. Quantum tunneling composites (QTCs) are composite materials made from conductive filler particles combined with an elastomeric binder, typically silicone rubber. The unique method of combining these raw materials results in a composite material which exhibits significantly different electrical properties when compared with any other electrically conductive material. QTC has the unique ability to smoothly change from an electrical insulator to a metal-like conductor when placed under pressure. While in an unstressed state, the QTC material is a near-perfect insulator. With any form of deformation, the material starts to conduct and with sufficient pressure metal-like conductivity levels can be achieved. The deformation required to produce a significant (factor of 10) change in resistance is significantly less for QTC than for carbon composites. QTC can be used to detect even very small changes due to compression, tension or other stresses.

Figure 2:
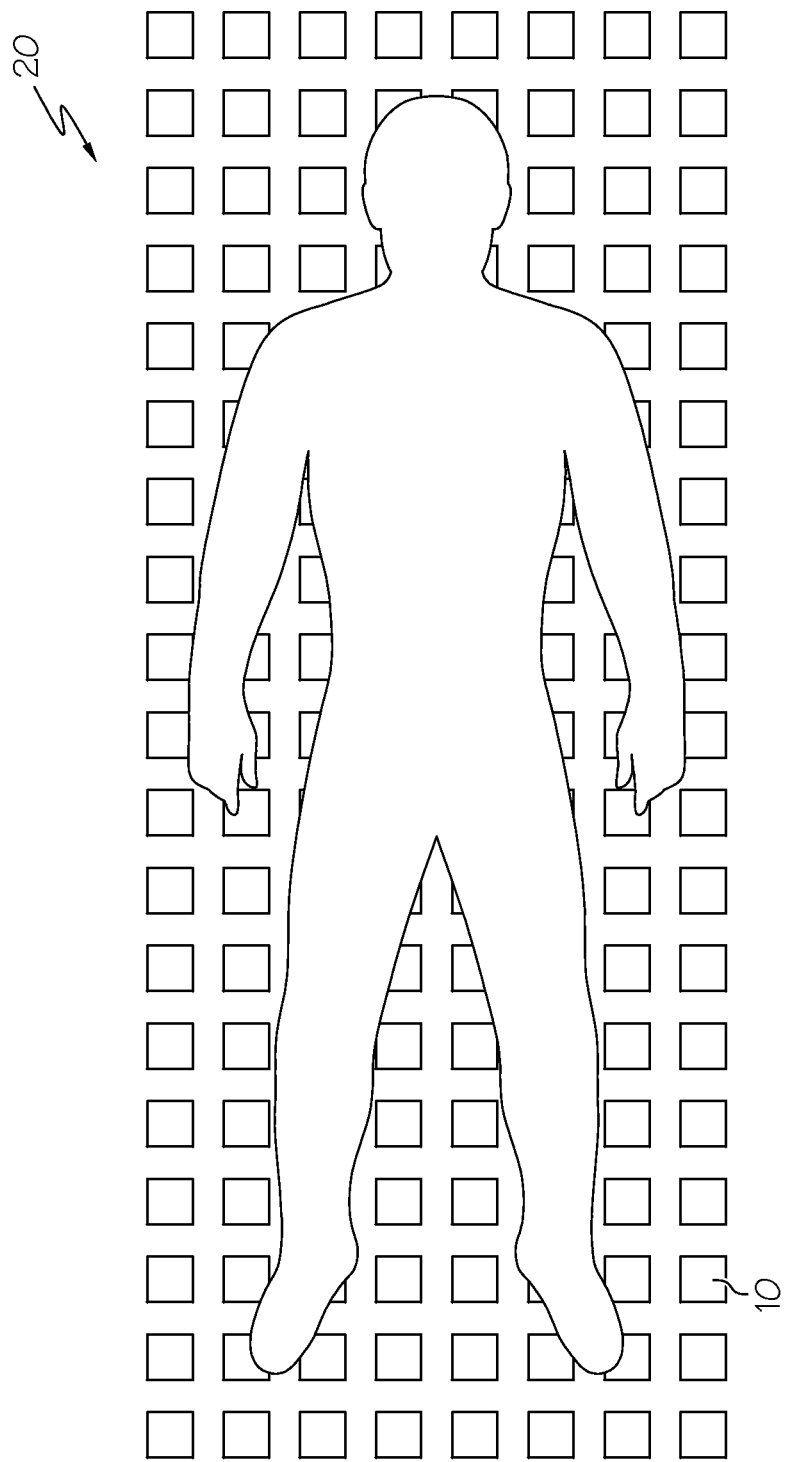
FIG. 2 illustrates an example of an array of RFID tags being used to monitor pressure.

FIG. 2 illustrates an embodiment in which an array of sensor devices 20 disposed in a predetermined (e.g., grid-like) pattern on a mat can be used to monitor pressure associated with a person lying in a bed or seated in a chair. Each tag in the array is in communication with the reader system. Each individual tag 10 can carry its own calibration, such as its sensitivity at zero pressure, or the array 20 can be calibrated before the patient is placed onto the bed to "zero" the results. In some embodiments, the RFID mat can be disposable. In other applications of the RFID mat, the sensing devices can be located on the mat in other patterns.

Figure 3:
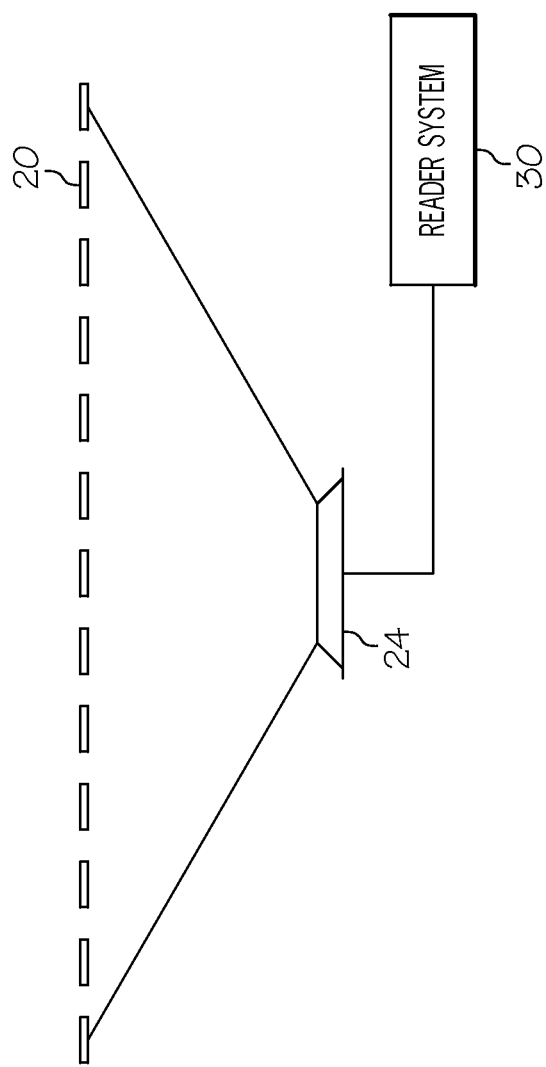
FIG. 3 illustrates an option for communicating with an array of RFID tags in an exemplary embodiment.

FIG. 3 illustrates one option for communicating with a group or array of RFID tags 20. In this embodiment, either a near field or a far field antenna 24 illuminates a group of tags 20 allowing the reader system 30 to measure the sensor data at each node. In an industrial system, the RFID reader is a unit containing the RF communication circuitry, logic and software needed to communicate with an RFID tag, and is generally equipped with an RF connection to an external antenna and some form of power and data communication connections. The reader unit can be "'dumb," in that its actions at a low level are controlled via the data communication interface, or can be "smart" wherein a program script is running on its internal processing system and it does not require communications to a host system in real time to perform a task.

Having a reader designed to operate with an external antenna provides greater flexibility in optimizing the antenna for the required task. For example, in a portal through which goods on pallets are being moved, a far field antenna with a defined static radiation pattern may be suitable, whereas for an application at a point of sale in a store, a near field antenna may be more suitable as it provides a defined range.

Figure 4:
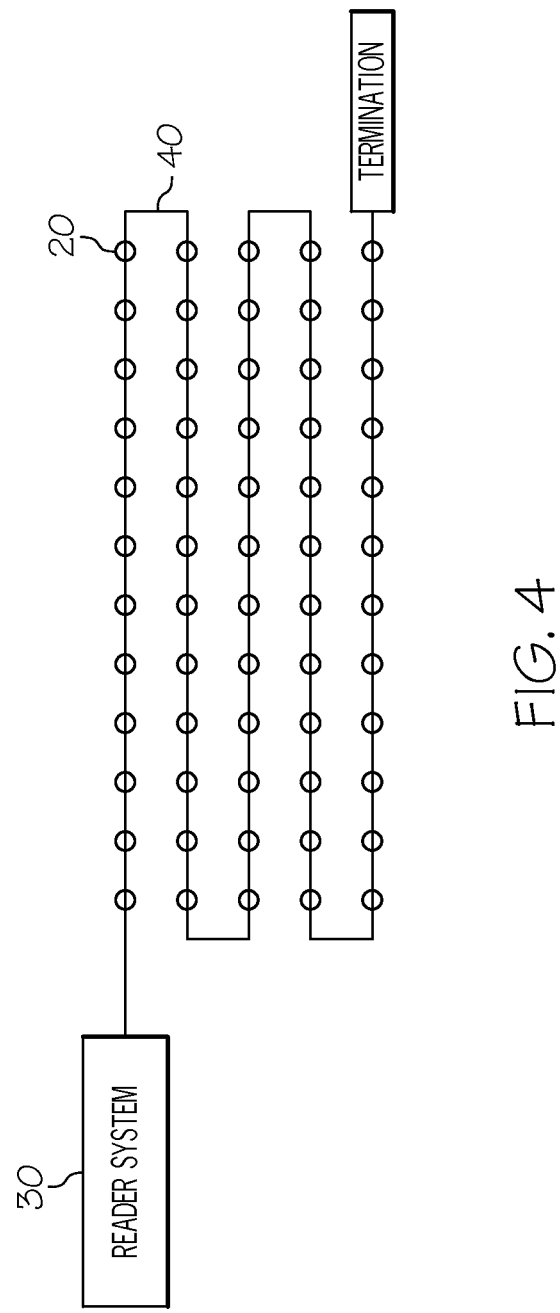
FIG. 4 illustrates another embodiment for reading a group of RFID sensor tags.

FIG. 4 illustrates another approach to reading a group of RFID sensor tags 20. In this embodiment, a transmission line distributed antenna structure 40, such as microstrip, twin wire line, or stripline can be used to couple the array of sensor tags 20 to the reader device 30. The array of sensor tags 20 is located in proximity to the transmission structure 40. A stripline transmission line medium uses a flat strip of metal sandwiched between two parallel ground planes. Stripline, which could be made from a low cost foil, has an advantage in that the coupling is independent of other parameters, such as the dielectric effects from a person in proximity, while still responding to the sensed parameter. In the embodiment of FIG. 4, a single transmission line distributed antenna structure 40 can connect the plurality of sensor devices 20 to a single port of an RFID reader system 30.

In the present context, the term "transmission line" is used to cover a large number of different structures essentially designed to transmit AC energy from one point to another with minimum loss. For some structures, such as a microstrip line, or a coaxial line with a non-continuous shield, there is an associated near magnetic and electric field to which an RFID tag can couple when placed in proximity. The transmission line is a form of near field antenna.

Figure 5:
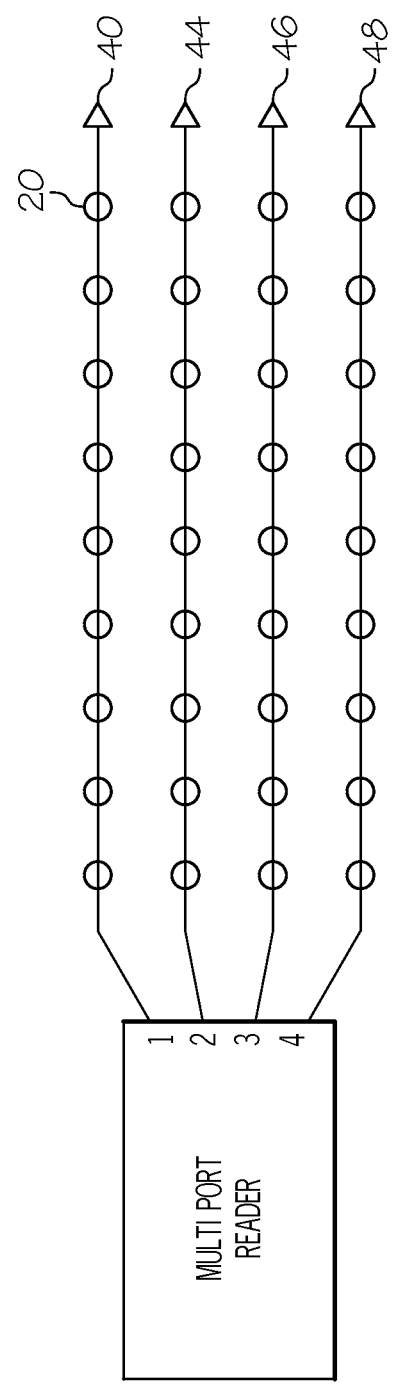
FIG. 5 illustrates an array of a RFID sensor tags in proximity to a series of transmission lines driven by the reader system in an exemplary embodiment.

In the embodiment of FIG. 5 the array of sensor tags 20 includes a series of different transmission lines 42, 44, 46, 48 connected to separate ports 1, 2, 3, 4 of a multi-port reader system, respectively. The sensor tags 20 can be located on the mat in proximity to the series of transmission lines 42, 44, 46, 48.

Figure 6:
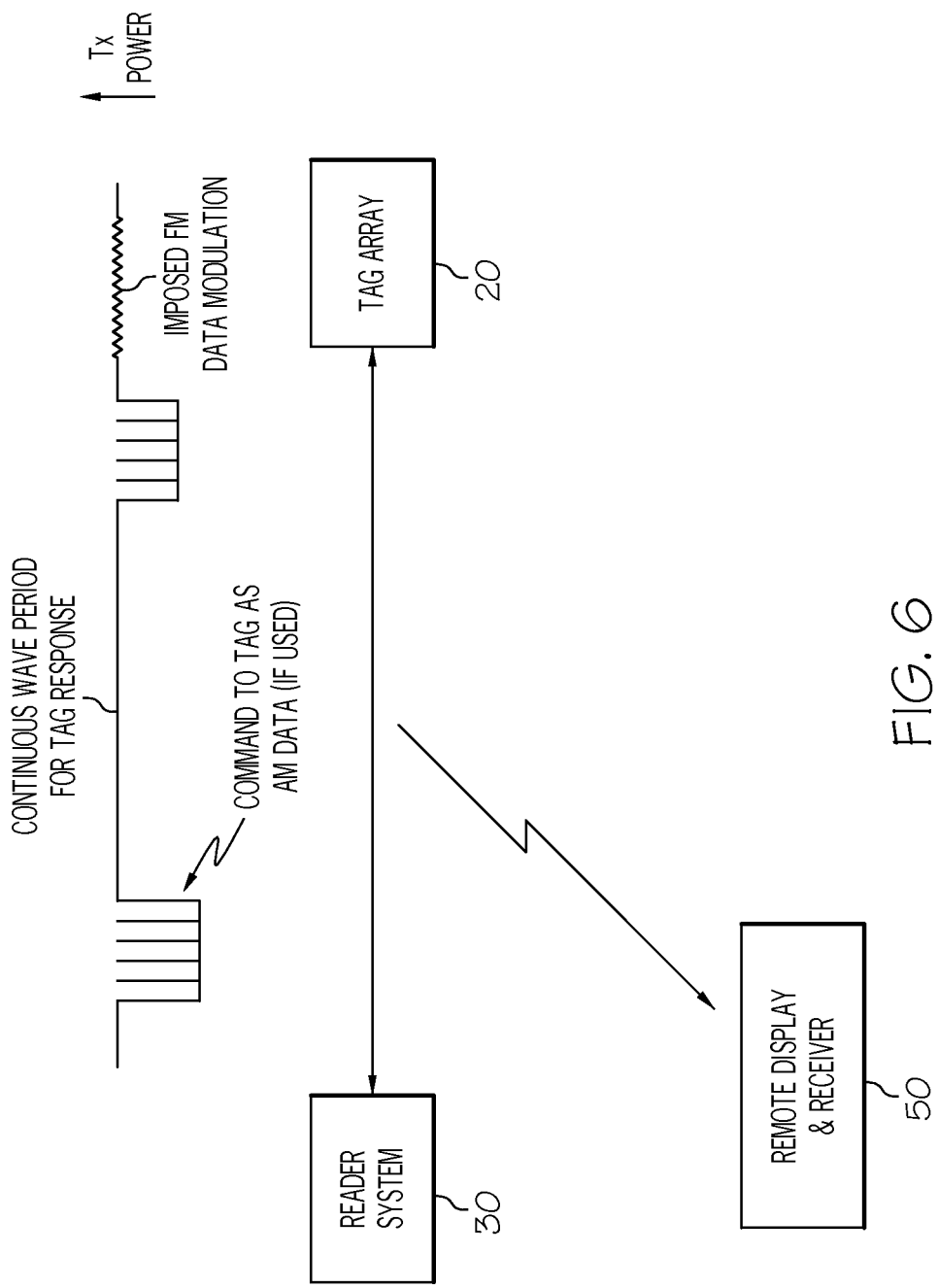
FIG. 6 illustrates use of a reader system to relay identification of tags as seen by a host system in an exemplary embodiment.

FIG. 6 illustrates an embodiment in which the reader system 30 can be adapted to self-transmit the ID of the tags 10 read at a given power level to a host computer system including remote display and receivers 50, minimizing processing power and power consumption at the reader 30. For reader "talks first" protocols, the communication to the tag 10 uses a series of data messages from the reader 30 to the individual tag 10, usually in the form of amplitude (AM) modulation of the RF energy, to operate a contention access protocol and allow the tag 10 to transmit its ID by backscatter modulation in continuous wave (CW) periods of the RF energy. In this embodiment, the reader 30 interrogates the chips 18 (FIG. 1) and obtains their ID, and then frequency (FM) modulates the next period of CW with the ID of the tags 10 that it has detected. As coherent detection is used in the reader 30, the FM modulation has no effect on the tag 10 to reader 30 communication. However, a remote host computer system including a display and wireless transceiver 50 will obtain the ID's of all tags 10 that responded to the reader 30 by simply listening.

Figure 7:
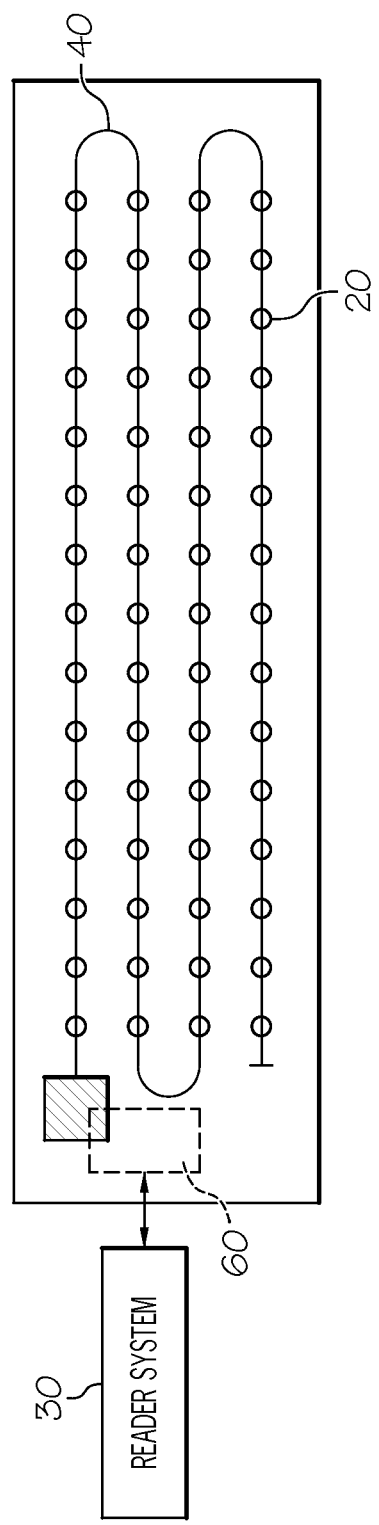
FIG. 7 illustrates a system incorporating a near field coupler to link a sensor array to a reader system in an exemplary embodiment.

FIG. 7 illustrates an embodiment having a structure wherein a near field coupler 60 can be used to connect the reader system 30 to the transmission line 40 and sensor tag array 20 in the disposable mat or covering. In this way a direct electrical connection between the reader system 30 and the mat is avoided, and the reader system 30 can be reused multiple times with the mat disposed of as required. Near field coupler 60 is essentially a way of connecting the distributed near field antenna (i.e., transmission line 40) incorporated into the disposable mat with the reader. This non-contact method, wherein the RF energy is bi-directionally coupled to the mat, is more reliable than physical connectors, such as coaxial connectors, and does not require precise alignment between the coupler 60 which is deployed in a fixed part of the system, for example, the bed or chair, and the array of sensing elements 20 built into the mat.

As described herein, the sensing material loading the antenna can have a mixture of dielectric and magnetic properties. In the disclosed embodiments, the resistivity of the material may be pressure-dependent, however, the real part of the dielectric constant could be a function of temperature. For example, depending on the antenna design, the real part of the dielectric constant could alter the operating frequency response of the antenna where the material resistivity primarily affects the sensitivity. Other factors that could be sensed include the presence of a dielectric liquid such as urine, light, or any other parameter that would allow some factor related to the condition or position of a person on the mat to be determined.

The corresponding structures, materials, acts, and equivalents of all means plus function elements in any claims below are intended to include any structure, material, or acts for performing the function in combination with other claim elements as specifically claimed. Those skilled in the art will appreciate that many modifications to the exemplary embodiments are possible without departing from the scope of the present invention.

In addition, it is possible to use some of the features of the embodiments disclosed without the corresponding use of the other features. Accordingly, the foregoing description of the exemplary embodiments is provided for the purpose of illustrating the principles of the invention, and not in limitation thereof, since the scope of the present invention is defined solely by the appended claims.

What is claimed:

1. An RFID sensing system comprising:
    an array of sensing elements disposed on a surface of a mat, wherein each sensing element includes an RFID microchip, an antenna operatively coupled to the microchip, and a pressure-sensitive material disposed on at least the antenna;
    an RFID reader for interrogating the array of sensing elements; an antenna operatively coupled to the reader for communicating with each sensing element disposed on the mat;
    wherein each sensing element in the array, in response to an interrogation signal, transmits a signal to the reader via the coupled antenna when a subject placed on the mat compresses the pressure-sensitive material for the sensing element,
    wherein the transmitted signal corresponds to the change in pressure attributable to the placement of the subject on the mat,
    wherein the reader determines the change in pressure by altering the output power and determining the power level at which an identifier ID associated with a sensing element starts to read.

2. The RFID sensing system of claim 1, wherein the pressure-sensitive material comprises a conductive foam.

3. The RFID sensing system of claim 2, further comprising a pressure-sensitive overlaminate material separating the sensing element antenna from the conductive foam.

4. The RFID sensing system of claim 1, wherein the pressure-sensitive material comprises a quantum tunneling composite.

5. The RFID sensing system of claim 1, wherein the antenna operatively coupled to the reader comprises a near field antenna.

6. The RFID sensing system of claim 1, wherein the antenna operatively coupled to the reader comprises a far field antenna.

7. The RFID sensing system of claim 2, wherein the resistance of the conductive foam decreases as the foam is compressed.

8. The RFID sensing system of claim 2, wherein the conductive foam is coated with a plurality of conductive particles.

9. The RFID sensing system of claim 2, wherein the conductive foam is coated with carbon.

10. The RFID sensing system of claim 1, wherein the antenna operatively coupled to the microchip comprises a structure operating at an ultra high frequency (UHF).

11. The RFID sensing system of claim 1, wherein the signal transmitted by each sensing element represents a change in sensitivity for the sensing element resulting from absorption of energy at an operating frequency of the sensing element caused by compression of the pressure-sensitive material.

12. An RFID sensing system comprising:
an array of sensing elements disposed on a surface of a mat, wherein each sensing element includes an RFID microchip, an antenna operatively coupled to the microchip, and a pressure-sensitive material disposed on at least the antenna;
an RFID reader for interrogating the array of sensing elements;
a transmission line coupled to a port of the reader and to each element in the array of sensing elements;
wherein each sensing element in the array, in response to an interrogation signal, transmits a signal to the reader via the coupled transmission line when a subject placed on the mat compresses the pressure-sensitive material for the sensing element,
wherein the transmitted signal corresponds to the change in pressure attributable to the placement of the subject on the mat,
wherein the reader determines the change in pressure by altering, the output power and determining the power level at which an identifier ID associated with a sensing element starts to read.

13. The RFID sensing system of claim 12, wherein the pressure-sensitive material comprises a conductive foam.

14. The RFID sensing system of claim 13, further comprising a pressure-sensitive over laminate material separating the sensing element from the conductive foam.

15. The RFID sensing system of claim 12, wherein the pressure-sensitive material comprises a quantum tunneling composite.

16. The RFID sensing system of claim 12, wherein the signal transmitted by each sensing element represents a change in sensitivity for the sensing element resulting from absorption of energy at an operating frequency of the sensing element caused by compression of the pressure-sensitive material.

17. The RFID sensing system of claim 12, wherein the transmission line comprises any one of a microstrip, a twin wire line, and a stripline.

18. An RFID sensing system comprising:
an array of sensing elements disposed on a surface of a mat, wherein each sensing element includes an RFID microchip, an antenna operatively coupled to the microchip, and a pressure-sensitive material disposed on at least the antenna;
a multi-port RFID reader for interrogating the array of sensing elements;
a plurality of transmission lines each coupled to a separate port of the reader and to an associated plurality of sensing elements in the array of sensing elements;
wherein each sensing element in the array, in response to an interrogation signal, transmits a signal to a reader port via the associated transmission line when a subject placed on the mat compresses the pressure-sensitive material for the sensing element,
wherein the transmitted signal corresponds to the change in pressure attributable to the placement of the subject on the mat,
wherein the reader determines the change in pressure by altering the output power and determining the power level at which an identifier ID associated with a sensing element starts to read.

19. The RFID sensing system of claim 12, wherein the signal transmitted by each sensing element represents a change in sensitivity for the sensing element resulting from absorption of energy at an operating frequency of the sensing element caused by compression of the pressure-sensitive material.

20. The RFID sensing system of claim 12, wherein each transmission line comprises any one of a microstrip, a twin wire line, and a stripline.

21. An RFID sensing system comprising:
an array of sensing elements disposed on a surface of a mat, wherein each sensing element includes an RFID microchip, an antenna operatively coupled to the microchip, and a pressure-sensitive material disposed on at least the antenna;
an RFID reader for interrogating the array of sensing elements;
a fixed near field coupler disposed in proximity to the mat for linking the array of sensing elements with the reader via a transmission line disposed on the mat;
wherein each sensing element in the array, in response to an interrogation signal, transmits a signal to the reader via the transmission line and near field coupler when a subject placed on the mat compresses the pressure-sensitive material for the sensing element,
wherein the transmitted signal corresponds to the change in pressure attributable to the placement of the subject on the mat~
wherein the reader determines the change in pressure by altering the output power and determining the power level at which an identifier ID associated with a sensing element starts to read.

22. The RFID sensing system of claim 21, wherein the pressure-sensitive material comprises a conductive foam.

23. The RFID sensing system of claim 22, further comprising a pressure-sensitive overlaminate material separating the sensing element antenna from the conductive foam.

24. The RFID sensing system of claim 21, wherein the pressure-sensitive material comprises a quantum tunneling composite.

25. The RFID sensing system of claim 21, wherein the signal transmitted by each sensing element represents a change in sensitivity for the sensing element resulting from absorption of energy at an operating frequency of the sensing element caused by compression of the pressure-sensitive material.

26. The RFID sensing system of claim 21, wherein the transmission line comprises any one of a microstrip, a twin wire line, and a stripline.

27. A method for sensing a parameter associated with an RFID sensing system comprising the steps of:
disposing an array of sensing elements on a surface of a mat, wherein each sensing element includes an RFID microchip, an antenna operatively coupled to the microchip, and a pressure-sensitive material disposed on at least the antenna;
interrogating the array of sensing elements using an RFID reader when a subject is placed on the mat compressing the pressure-sensitive material for the sensing element;
communicating with each sensing element disposed on the mat via an antenna operatively coupled to the reader; and
receiving a signal transmitted from each sensing element in the array via the antenna coupled to the reader in response to an interrogation signal,
wherein the transmitted signal corresponds to the change in pressure attributable to the placement of the subject on the mat,
wherein the reader determines the change in pressure by altering the output power and determining the power level at which an identifier ID associated with a sensing element starts to read.

28. The method for sensing a parameter of claim 27, wherein the pressure-sensitive material comprises a conductive foam.

29. The method for sensing a parameter of claim 28, further comprising the step of applying a pressure-sensitive overlaminate to separate the pressure-sensitive material from the conductive foam.

30. The method for sensing a parameter of claim 28, further comprising the step of coating the conductive foam with a plurality of conductive particles.

31. The method for sensing a parameter of claim 27, wherein the pressure-sensitive material comprises a quantum tunneling composite.

32. The method for sensing a parameter of claim 28, wherein the signal transmitted from each sensing element provides a change in sensitivity for the sensing element resulting from absorption of energy at an operating frequency of the sensing element caused by compression of the pressure-sensitive material.

33. The method for sensing a parameter of claim 32, wherein the operating frequency of the sensing element is an ultra high frequency (UHF).

34. The method for sensing a parameter of claim 32, further comprising the step of determining a power level at which an identification associated with the sensing element is read by the RFID reader.

35. The method for sensing a parameter of claim 32, further comprising determining a pressure at a point on the surface of the mat at which the sensing element is located using the change in sensitivity of the sensing element.

36. The method for sensing a parameter of claim 27, further comprising calibrating the sensitivity at each sensing element with no pressure placed on the mat surface.

37. The method for sensing a parameter of claim 27, wherein the step of communicating with each sensing element disposed on the mat comprises illuminating the sensing element by a near field antenna and enabling the reader to measure a plurality of sensor data at the sensing element.

38. The method for sensing a parameter of claim 27, wherein the step of communicating with each sensing element disposed on the mat comprises illuminating the sensing element by a far field antenna and enabling the reader to measure a plurality of sensor data at the sensing element.

39. The method for sensing a parameter of claim 27, further comprising communicating a series of data messages from the reader to the sensing element via an amplitude modulation of a continuous wave signal.

40. The method for sensing a parameter of claim 39, further comprising receiving an identification at the reader in a backscatter modulation of RF energy from each sensing element.

41. The method for sensing a parameter of claim 40, further comprising communicating the identification received from each sensing element from the reader to the sensing element via a frequency modulation of a continuous wave signal.

42. The method for sensing a parameter of claim 41, further comprising passively detecting the identification of each sensing element during the frequency modulation by a remote computer system.

43. A method for sensing a parameter associated with an RFID sensing system comprising the steps of:
disposing an array of sensing elements on a surface of a mat, wherein each sensing element includes an RFID microchip, an antenna operatively coupled to the microchip, and a pressure-sensitive material disposed on at least the antenna;
interrogating the array of sensing elements using an RFID reader when a subject is placed on the mat compressing the pressure-sensitive material for the sensing element;
communicating with each sensing element disposed on the mat via a transmission line operatively coupled to the reader and to at least a plurality of elements in the array of sensing elements; and
receiving a signal transmitted from each sensing element in the array via the transmission line in response to an interrogation signal,
wherein the transmitted signal corresponds to the change in pressure attributable to the placement of the subject on the mat,
wherein the reader determines the change in pressure by altering the output power and determining the power level at which an identifier ID associated with a sensing element starts to read.

44. The method for sensing a parameter of claim 43, further comprising the step of coupling a plurality of transmission lines to separate ports of a multi-port RFID reader, with each transmission line operatively coupled to an associated plurality of sensing elements in the array of sensing elements.

* * * * *